US007157416B2

(12) United States Patent
Becker et al.

(10) Patent No.: US 7,157,416 B2
(45) Date of Patent: Jan. 2, 2007

(54) STABILIZATION OF ENZYMES

(75) Inventors: Nathaniel T. Becker, Hillsborough, CA (US); Richard R. Bott, Burlingame, CA (US); Shauna L. Bowden, Mountain View, CA (US); Meng Hong Heng, Belmont, CA (US); Christian Paech, Daly City, CA (US); Antti V. Kosola, Kirkkonummi (FI)

(73) Assignee: Genencor International, Inc., Palo Alto, CA (US)

( * ) Notice: Subject to any disclaimer, the term of this patent is extended or adjusted under 35 U.S.C. 154(b) by 186 days.

(21) Appl. No.: 10/333,176

(22) PCT Filed: Jul. 20, 2001

(86) PCT No.: PCT/US01/23076

§ 371 (c)(1),
(2), (4) Date: Jan. 16, 2003

(87) PCT Pub. No.: WO02/08398

PCT Pub. Date: Jan. 31, 2002

(65) Prior Publication Data

US 2003/0216277 A1    Nov. 20, 2003

(51) Int. Cl.
*C11D 9/50*  (2006.01)
*C11D 7/42*  (2006.01)
*C12N 9/96*  (2006.01)

(52) U.S. Cl. .................. 510/393; 510/303; 510/305; 435/188; 424/94.1; 424/94.3

(58) Field of Classification Search .............. 510/300, 510/305, 393, 303; 435/221, 264, 188; 424/94.1, 424/94.3
See application file for complete search history.

(56) References Cited

U.S. PATENT DOCUMENTS

| 4,152,418 A | * | 5/1979 | Pader ......................... 424/50 |
| 5,155,033 A | | 10/1992 | Estell et al. ................ 435/221 |
| 5,185,258 A | | 2/1993 | Caldwell et al. ........... 435/220 |
| RE34,606 E | | 5/1994 | Estell et al. ................ 435/222 |
| 5,346,823 A | | 9/1994 | Estell et al. ................ 435/222 |
| 5,679,630 A | * | 10/1997 | Baeck et al. ................ 510/305 |
| 5,700,676 A | | 12/1997 | Bott et al. ................... 435/221 |
| 5,718,895 A | * | 2/1998 | Asgharian et al. ......... 424/94.1 |
| 5,763,257 A | | 6/1998 | Bott et al. ................... 435/221 |
| 6,218,165 B1 | | 4/2001 | Estell et al. ................ 435/221 |
| 6,897,049 B1 | | 5/2005 | Estell et al. ................ 435/183 |

FOREIGN PATENT DOCUMENTS

| EP | 0 251 446 B1 | 12/1994 |
| EP | 0 451 244 B9 | 12/1998 |
| EP | 0130 756 B2 | 6/2000 |
| EP | 0 775 749 B1 | 6/2005 |

* cited by examiner

*Primary Examiner*—Douglas McGinty
*Assistant Examiner*—Preeti Kumar
(74) *Attorney, Agent, or Firm*—Genencor International, Inc.

(57) ABSTRACT

Enzyme-containing formulations having improved stability and enzymatic activity in liquid medium, comprising one or more protease enzymes produced from any *Bacillus* bacteria, at least about 5% alkali metal halide salt, and at least about 50% polyol. Also disclosed are methods for making such formulations.

12 Claims, No Drawings

STABILIZATION OF ENZYMES

BACKGROUND OF THE INVENTION

1. Field of the Invention

The present invention relates to enzyme compositions and liquid formulations including enzymes. Particularly, the invention relates to methods for stabilizing enzymes and to liquid formulations with the stabilized enzymes.

2. Background

The stabilization of enzymatic activity is a standing problem in all areas of technology where enzymes are likely to be applied. Stability in this sense includes resistance to decrease in enzymatic activity prior to usage, e.g., under storage conditions. Stabilization of enzymes in liquid formulations is particularly a problem For example, a pre-formulated liquid enzyme concentrate may sometimes be stored for weeks or months before eventually being blended into a final product (e.g., a personal care product, such as a hand cream; or a cleaning product, such as a liquid detergent). Similarly, formulated liquid products containing enzymes may sit in storage for lengthy periods of time before use, as well. For a variety of reasons, the activity of enzymes in liquid formulations typically decreases over time.

The prior art has attempted to deal with this problem. For example, organic compounds, such as sodium formate, and propylene glycol or glycerol are often added to liquid enzyme formulations. U.S. Pat. No. 4,318,818, Letton et al., issued Mar. 9, 1982, discloses liquid detergents containing enzymes and an enzyme-stabilizing system comprising calcium ions and a low molecular weight carboxylic acid or salt, preferably a formate. The composition preferably contains an anionic surfactant and a saturated fatty acid. U.S. Pat. No. 4,404,115, Tai, issued Sep. 13, 1983, discloses cleaning compositions containing enzymes, alkali metal pentaborate, al metal sulfite and a polyol. While somewhat effective, additives such as formate and other organic salts unfortunately are costly and, thus, significantly add to the expense of the liquid enzyme concentrate and final product. Further, there is in some instances a desire for formulations which are acceptable for food, pharmaceutical, or cosmetic use, and certain salts like sodium formate may not be acceptable or suitable for this purpose.

The use of inorganic salts as stabilization agents for enzymes is known in the art. For instance, U.S. Pat. No. 5,460,658, Nakagawa et al, issued Oct. 24, 1995, discloses an enzyme based contact lens cleaning solution said to be stabilized with a polyhydric alcohol (5–30%) and alkali metal salt (1–5%) combination. The Nakagawa et al. patent teaches that polyhydric alcohol levels are less than 30% to maintain enzyme activity in the contact lens solution application. Xylanase was stabilized with a polyol (2040%) and formate or potassium chloride (48%) as described in a study entitled "Developmnent of A Method for the Stabilization and Formulation of Xylanase from *Trichoderma* Using Experimental Design", R. Spencer Fisk and Curran Simpson, as reported in Studies in Organic Chemistry, vol. 47, Stability and Stabilization of Enzymes, Elsevier, edited by W. J. J. Van Den Tweel, A. Harder, R. M. Buitelaar, 1992. This study discloses the use of no more than 40% polyol to maintain xylanase activity.

A cosmetic formulation having an enzyme stabilized using a 30–99% water-binding polyol that is partially or totally complexed with acrylic or methacrylic polymer is described in U.S. Pat. No. 5,830,449, Afriat et al., issued Nov. 3, 1998, and U.S. Pat. No. 5,703,041, Afriat et al., issued Dec. 30, 1997. The cosmetic formulation may also include an inorganic salt (2 to 12%) as a secondary stabilizing agent.

Clearly, there is a continuing need for liquid formulations that contain enzymes which are stabilized and exhibit a high activity over time. Particularly, there is a need for protease stabilized liquid formulations that are easy to process, highly effective, inexpensive to produce relative to the previously used stabilizing formulations, relatively inactive until ultimately included as an ingredient in a selected application, and also useful for formulations that are well tolerated physiologically.

SUMMARY OF THE INVENTION

It has been discovered that the combination of a high level of alkali metal halide salts, such as sodium chloride (at least 4% or 5% w/w, or higher), in combination with a polyol solvent, such as glycerol, propylene glycol, sucrose, etc (30% w/w, or higher), provides a high level of thermal stability for protease (produced from *Bacillus* species, e.g., subtilisin) formulations.

One aspect of the present invention provides a method for stabilizing one or more enzymes in a liquid medium. In one embodiment, the method of the invention includes the step of formulating in the liquid medium a high level of an alkali metal halide salt in combination with a polyol solvent.

The alkali metal halide salt cap be, for example, sodium chloride, potassium chloride, and sodium or potassium fluoride or bromide. Lithium salts may also be used. Additionally, other inorganic salts, such as salts of sulfates or sulfites, carbonates, phosphates, silicates or nitrates may be used. One preferred embodiment contemplates at least between 4–12% (e.g., at least 4%, at least 5%, at least 6%, at least 7%, at least 8%, at least 9%, at least 10%, at least 11%, and/or at least 12%) sodium chloride. In one embodiment, the sodium chloride comprises between about 5–12%, preferably about 8–12% w/w, of the liquid formulation.

The polyol can be present, for example, at a level of at least 30%, at least 40%, at least 50%, at least 60%, at least 70%, at least 80%, at least 90%, and/or at least 95%. For example, one embodiment contemplates between 50 to 98% polyol, preferably between 55 and 95% polyol, preferably between 80 to 90% polyol, and most is preferably 50 to 80% polyol. Suitable polyols include, for example, glycerol, propylene glycol, sucrose, among others.

Among the various enzymes that can be stabilized by the teachings herein, one preferred enzyme is a protease, produced from *Bacillus* species, such as a subtilisin.

The liquid medium of the invention can be, for example, a liquid enzyme concentrate or a formulated product including at least one enzyme, such as a protease. In one embodiment, the liquid medium is a formulated product selected from the group consisting of personal care products, health care products, and cleaning/detergency products. The liquid medium can be used, for example, in formulating hand creams, liquid detergents, and the like.

Another aspect of the present invention provides a liquid formulation providing an enzyme-stabilizing environment. In one embodiment, the formulation includes one or more enzymes, a high level of an alkali metal salt, and a polyol solvent.

The alkali metal halide salt can be, for example, sodium chloride, potassium chloride, and sodium or potassium fluoride or bromide. Lithium salts also may be used. Additionally, other inorganic salts, such as salts of sulfates or sulfites, carbonates, phosphates, silicates or nitrates may be used. In one embodiment, the sodium chloride is present at a level of between 4–12% (e.g., at least 4%, at least 5%, at least 6%, at least 7%, at least 8%, at least 9%, at least 10%, at least 11%, up to and including 12%). In an exemplary formulation, the sodium chloride comprises about 8–12% w/w of the liquid formulation.

The polyol is preferably present, for example, at a level of at least 30%. Certain embodiments contemplate a polyol level of at least 30%, at least 40%, at least 50%, at least 60%, at least 70%, at least 80%, at least 90%, and/or at least 95%. One embodiment contemplates between 50 to 98% polyol, preferably between 55 and 95% polyol, preferably between 80 to 90% polyol, and most preferably 50 to 80 polyol. Suitable polyols include, for example, glycerol, propylene glycol, sucrose, among others.

Among the one or more enzymes that are stabilized in the formulation, one embodiment contemplates inclusion of a protease produced from *Bacillus* species, preferably a subtilisin.

In one embodiment, the liquid formulation is a liquid enzyme concentrate or a formulated product including at least one enzyme, such as a protease produced from *Baccillus* species, such as a subtilisin. The liquid formulation can be, for example, a formulated product such as a personal care product, health care product, a cleaning product, a detergency product, among others.

Still a further aspect of the present invention provides a stabilized liquid enzyme formulation, including: (i) a protease, such as subtilisin; (ii) at least 5% w/w of an alkali metal halide salt, such as sodium chloride, potassium chloride, sodium or potassium fluoride or bromide, or lithium salts. Additionally, other inorganic salts, such as salts of sulfates or sulfites, carbonates, phosphates, silicates or nitrates may be used; and (iii) at least 30% w/w of a polyol solvent, such as glycol. Preferably, the formulation includes a subtilisin which is stabilized to exhibit at least about 98% activity remaining after 22 days at 37 degrees C. In one embodiment, the stabilized subtilisin includes an amino acid substitution at position 217 (e.g., Y217L).

These and other features, aspects and advantages of the present invention will become apparent from the following detailed description, in conjunction with the appended claims.

DETAILED DESCRIPTION OF THE INVENTION

The present invention provides methods for stabilizing enzymes and liquid formulations including stabilized enzymes utilizing a polyol and an alkali metal halide salt.

Percentages herein are expressed as a percentage by weight of the liquid formulation.

The inventors hereof have determined that the combination of a high level of an alkali metal halide salt (e.g., sodium chloride) in combination with a polyol solvent (e.g., glycol) provides a high level of thermal stability for liquid enzyme (e.g., proteases produced from *Bacillus* species) formulations.

Generally, formulations of the present invention include at least about 30% polyol or polyhydric alcohol; for example between from about 50 to about 98%, between from about 50 to about 95%, between from about 80 to about 90% polyol, and/or between from about 50–80% polyol. An exemplary liquid formulation suitable for inclusion in personal care applications, as contemplated herein, includes between from about 50% to about 80% glycerol. Other suitable polyols include, and are not limited to, propylene glycol, ethylene glycol, sorbitol, mannitol, erythritol, dulcitol and inositol. Such a liquid formulation can be further formulated into, for example, a hand cream, or the like. A liquid formulation for liquid detergent applications, as contemplated herein, includes between from about 33 to about 40% propylene glycol. Another exemplary liquid formulation for personal care application includes about 60% glycerol. The polyol level is approximately 50–80% to produce a compound having relatively inactive enzymes until such compound ultimately is included in a specific application.

Formulations of the present invention include at least about 5% of an alkali metal halide salt, such as sodium chloride, potassium chloride, and sodium or potassium fluoride or bromide, or lithium salts. Additionally, other inorganic salts, such as salts of sulfates or sulfites, carbonates, phosphates, silicates or nitrates may be used. In one preferred embodiment, the alkali halide metal salt is sodium chloride. The sodium chloride can be present, for example, at a level of at least about 5%, at least about 6%, at least about 7%, at least about 8%, at least about 9%, at least about 10%, at least about 11%, and/or at least about 12%. In one embodiment, a liquid enzyme formulation includes between from about 5% to about 12% sodium chloride (e.g., preferred at about 8% sodium chloride). In another preferred embodiment, the liquid enzyme formulation includes about 10% sodium chloride.

Preferred enzymes include those enzymes capable of hydrolyzing substrates. Such enzymes, which are known as hydrolases, include, but are not limited to, proteases (bacterial, fungal, acid, neutral or alkaline), amylases (alpha or beta), lipases, cellulases and mixtures thereof. Preferred proteases are also those described in US Re. 34,606 and EP 0 130 756, EP 251,446, EP 451,244, and EP 775,749, and incorporated herein by reference. Other preferred proteases are described in U.S. Pat. Nos. 6,218,165, 5,284,791, 5,700, 676, 5,185,258, 5,155,033, 5,346,823, 5,763,257 and U.S. patent application Ser. No. 09/768,080, filed Feb. 8, 2000, titled Proteins Producing An Altered Immunogenic Response And Methods Of Making And Using The Same, describing protease mutants having an altered T-cell epitope. One preferred protease is available under the trade name Multifect, from Genencor International, Inc. Other preferred proteases include Purafect and Properase, from Genencor International, Inc. or Savinase, Esperase, Alcalase available from Novozymes A/S. Preferred proteases are those produced from any *Bacillus* species and include mutants which retain their *bacillus* protease-like structure and function. Other enzymes that can be used in the present invention include oxidases, peroxidases, transferases, dehydratases, reductases, hemicellulases and isomerases, among others. One or more enzymes may be included in the formulations of the present invention.

The stabilized liquid enzyme formulations of the present invention can be applied in a variety of fields, including the fields of personal care (e.g., protease for use in hand creams, and the like), and cleaning (e.g., protease for use in liquid detergents, and the like), among others. For example, the liquid enzyme formulations can be liquid enzyme concentrates which are useful for further formulation into final products, and/or they can be final formulated products, such as skin creams, lotions, liquid soaps, liquid detergents, etc.

Liquid enzyme formulations of the present invention are particularly effective at stabilizing enzymes during storage, within a temperature range of between from about 20 to about 40 degrees Celsius, e.g., at or around room temperature (22–25 degrees Celsius).

EXAMPLES

The following examples are illustrative and are not intended to limit the invention.

Example 1

Subtilisin BPN' Y217L was formulated at 5–7 gE/l in a base of 80–90% glycerol, 1 mM KH2PO4 at pH 5.0. The method of formulation generally involves the following: the 1 mM CaCl$_2$ reagent was added to the glycerol reagent followed by the addition of the selected enzyme. Water was then added and the resulting mixture was allowed to dissolve overnight at 4° C. The selected salt concentration was prepared by dissolving the salt in 1 M NaOAC prior to addition to the dissolved enzyme. Next, 3% CP carbon was added to the enzyme salt combination and the resulting compound was mixed at 22° C. for approximately 6 hours. Next, the compound was filtered and the resulting solution was stored for the stability studies set out below.

As shown in Table 1, the formulation was tested without further stabilization and with stabilization utilizing three stabilizers (sodium acetate, sodium chloride, and sodium formate).

TABLE 1

Stability Study 1

Basic Conditions for all samples
 * 50 ppm Ca2+          10 g enzyme solution
 * Temperature 25 C./37 C.

| Experiments | | | Product Activity |
|---|---|---|---|
| B0 KH2PO4 10 mM @ pH 5.0 before additions; 10% | Sodium Acetate; 8% | Glycerol; 82% | 6.75 gE/l |
| B1 KH2PO4 10 mM @ pH 5.0 before additions; 10% | Sodium Chloride; 8% | Glycerol; 82% | 6.75 gE/l |
| B2 KH2PO4 10 mM @ pH 5.0 before additions; 10% | Sodium Formate; 8% | Glycerol; 82% | 6.75 gE/l |
| B3 KH2PO4 10 mM @ pH 5.0 before additions; 10% | None | Glycerol; 90% | 6.75 gE/l |
| B4 KH2PO4 10 mM @ pH 5.0 before additions; 10% | None | Glycerol; 90% | 3.37 gE/l |
| B5 KH2PO4 10 mM @ pH 5.0 before additions; 10% | None | Glycerol; 45%/Propylene Glycol; 45% | 6.75 gE/l |
| B6 KH2PO4 10 mM @ pH 5.0 before additions; 10% | None | Propylene Glycol; 90% | 6.75 gE/l |
| B7 KH2PO4 10 mM @ pH 5.0 after additions; 10% | None | Glycerol; 90% | 6.75 gE/l |
| B8 KH2PO4 10 mM @ pH 5.5 before additions; 10% | None | Glycerol; 90% | 6.75 gE/l |

Activity levels for all of the above formulations were monitored as exhibited by the data of Table 2, which demonstrates that sodium chloride is a very effective agent for stabilization of subtilisin (note, in particular, B 1). Remaining enzyme activity at 22 days utilizing the three stabilizers as shown was between 96–98% as compared to a value of only 81% in the remaining formulations that did not include sodium acetate, sodium chloride or sodium formate.

TABLE 2

37° C.
Subtilisin Stability Study
Activities by AAPF-pNA Assay in ΔAU min$^{-1}$ml$^{-1}$

| | Buffer | | | | | | | | |
|---|---|---|---|---|---|---|---|---|---|
| Day | 0 | 1 | 2 | 3 | 4 | 5 | 6 | 7 | 8 |
| 0 | 206 | 211 | 233 | 229 | 112 | 234 | 204 | 200 | 204 |
| 1 | 212 | 216 | 239 | 238 | 113 | 238 | 214 | 171 | 214 |
| 6 | 205 | 210 | 228 | 214 | 98 | 217 | 177 | 161 | 198 |
| 22 | 196 | 206 | 224 | 185 | 49 | 179 | 109 | 142 | 160 |
| 41 | 186 | 208 | 212 | 150 | 11 | 163 | 62 | 116 | 138 |
| 66 | 186 | 205 | 202 | 129 | 7 | 132 | 32 | 33 | 113 |
| 94 | 183 | 192 | 183 | | | | | | 88 |

| | Activity left % | | Buffer | | | | | | |
|---|---|---|---|---|---|---|---|---|---|
| Day | B0 | B1 | B2 | B3 | B4 | B5 | B6 | B7 | B8 |
| 0 | 100 | 100 | 100 | 100 | 100 | 100 | 100 | 100 | 100 |
| 1 | 103 | 102 | 102 | 104 | 101 | 102 | 105 | 85 | 105 |
| 6 | 100 | 100 | 98 | 94 | 88 | 93 | 87 | 80 | 97 |
| 22 | 96 | 98 | 96 | 81 | 43 | 77 | 54 | 71 | 78 |

TABLE 2-continued

37° C.
Subtilisin Stability Study
Activities by AAPF-pNA Assay in ΔAU min⁻¹ml⁻¹

| 41 | 91 | 99 | 91 | 66 | 10 | 70 | 30 | 58 | 67 |
|----|----|----|----|----|----|----|----|----|----|
| 66 | 91 | 97 | 87 | 57 | 6  | 57 | 16 | 16 | 55 |
| 94 | 89 | 91 | 79 |    |    |    |    |    | 43 |

The 8% NaCl sample was found to have high stability (over 98% activity remaining after 22 days at 37 degrees C. and 100% after 23 days at 37 degrees C.). The data further demonstrates that a high activity level (at least 90%) remained in the presence of sodium chloride out to 94 days.

Table 3 below represents the same example as above conducted at 25° C.

TABLE 3

25° C.
Subtilisin Stability Study
Activities by AAPF-pNA Assay in ΔAU min⁻¹ml⁻¹

| | Buffer | | | | | | | | |
|---|---|---|---|---|---|---|---|---|---|
| Day | 0 | 1 | 2 | 3 | 4 | 5 | 6 | 7 | 8 |
| 0  | 206 | 211 | 233 | 229 | 112 | 234 | 204 | 200 | 204 |
| 2  | 205 | 216 | 223 | 227 | 108 | 227 | 200 | 184 | 197 |
| 23 | 204 | 212 | 242 | 214 | 94  | 223 | 188 | 166 | 203 |
| 30 | 200 | 213 | 220 | 214 | 85  | 215 | 182 | 153 | 197 |
| 65 | 201 | 206 | 227 | 192 | 40  | 187 | 158 | 135 | 174 |
| 94 | 189 | 197 | 222 |     |     |     |     |     | 158 |

| | Activity left % | | | Buffer | | | | | |
|---|---|---|---|---|---|---|---|---|---|
| Day | B0 | B1 | B2 | B3 | B4 | B5 | B6 | B7 | B8 |
| 0  | 100 | 100 | 100 | 100 | 100 | 100 | 100 | 100 | 100 |
| 2  | 100 | 102 | 96  | 99  | 97  | 97  | 98  | 92  | 96  |
| 23 | 99  | 101 | 104 | 93  | 84  | 95  | 93  | 83  | 99  |
| 30 | 97  | 101 | 94  | 93  | 76  | 92  | 90  | 77  | 97  |
| 65 | 98  | 98  | 97  | 84  | 35  | 80  | 78  | 68  | 77  |
| 94 | 92  | 93  | 95  |     |     |     |     |     | 77  |

Example 2 illustrates the results of a study designed to increase the commercial desirability of liquid enzyme formulations and to facilitate manufacturing of such formulations. Accordingly, Example 2 illustrates the surprising results achieved by reducing the concentration of glycerol and increasing the concentration of salt in the formulation.

Subtilisin BPN' Y217L was formulated as set out in Table 4 below in a base of 70–82% glycerol, 1 mM KH2PO4.

TABLE 4

Stability Study 2
Basic Conditions for all samples

* 50 ppm Ca2+          10 g enzyme solution
* Temperature 25 C./37 C.

| Form # | Enzyme Buffer | Salt** (g) | Salt Type | Glycerol** (g) | Target Enzyme Activity (mg/mL) | Enzyme (wt/wt %) | Final Form Density |
|---|---|---|---|---|---|---|---|
| B1  | 10 mM K-Phos, ph 5.0 | 8  | NaOAC      | 82 | 6.75 | 0.54  | 1.25 |
| B2  | 10 mM K-Phos ph 5.0  | 8  | NaCl       | 82 | 6.75 | 0.54  | 1.25 |
| B3  | 10 mM K-Phos ph 5.0  | 8  | NaOAC.3H2O | 82 | 1.3  | 0.104 | 1.25 |
| B4  | 10 mM K-Phos ph 5.5  | 12 | NaOAC.3H2O | 70 | 1.3  | 0.104 | 1.25 |
| B5  | 10 mM K-Phos ph 5.5  | 8  | NaCl       | 82 | 1.3  | 0.104 | 1.25 |
| B6  | 10 mM K-Phos ph 5.5  | 6  | NaCl       | 82 | 1.3  | 0.104 | 1.25 |
| B7  | 10 mM K-Phos ph 5.5  | 8  | NaCl       | 70 | 1.3  | 0.104 | 1.25 |
| B8  | 10 mM K-Phos ph 5.5  | 10 | NaCl       | 60 | 1.3  | 0.104 | 1.25 |
| B9  | 100 mM K-Phos ph 5.5 | 6  | NaCl       | 62 | 1.3  | 0.104 | 1.25 |
| B10 | 100 mM K-Phos ph 5.5 | 8  | NaCl       | 62 | 1.3  | 0.104 | 1.25 |

TABLE 4-continued

Stability Study 2
Basic Conditions for all samples

| | | | | | | | |
|---|---|---|---|---|---|---|---|
| B11 | 100 mM K-Phos ph 5.5 | 8 | NaCl | 70 | 1.3 | 0.104 | 1.25 |
| B12 | 100 mM K-Phos ph 5.5 | 10 | NaCl | 60 | 1.3 | 0.104 | 1.25 |
| B13 | 100 mM K-Phos ph 5.5 | 8 | NaOAC.3H2O | 82 | 1.3 | 0.104 | 1.25 |
| B14 | 100 mM K-Phos ph 5.5 | 12 | NaOAC.3H2O | 70 | 1.3 | 0.104 | 1.25 |

As shown by the surprising data of Table 5 below, a stable glycerol/salt formulation that is easily manufactured may be achieved by increasing the salt concentration thereby enabling a reduction in the amount of glycerol in the formulation. Table 5 illustrates that a 60% glycerol and 10% salt formulation is exceptionally stable.

TABLE 5

Subtilisin Stability Study: 25° C.
Activities by AAPF-pNA Assay in $\Delta AU\ min^{-1}ml^{-1}$

| Day | Buffer 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| 0 | 323 | 327 | 63.3 | 63.7 | 63.8 | 66.4 | 63.4 | 66.5 | 65.3 | 66.9 | 65.4 | 63.5 | 64.9 | 63.2 |
| 118 | 310 | 327 | 63.6 | 61.4 | 66.9 | 60.9 | 61.7 | 66.9 | 60.9 | 63.2 | 66.4 | 64.4 | 63.8 | 62.6 |
| 174 | 320 | 336 | 65.9 | 63.7 | 62.6 | 59.1 | 63.6 | 68.6 | 61.7 | 64.6 | 64.1 | 66.8 | 65.6 | 63.7 |
| 279 | 301 | 301 | 57.7 | 59.9 | 51.8 | 50.8 | 62.6 | 62.1 | 53.8 | 54.8 | 59.9 | 59.4 | 57.4 | 59.0 |

| % Original Activity | Buffer B1 | B2 | B3 | B4 | B5 | B6 | B7 | B8 | B9 | B10 | B11 | B12 | B13 | B14 |
|---|---|---|---|---|---|---|---|---|---|---|---|---|---|---|
| 0 | 100 | 100 | 100 | 100 | 100 | 100 | 100 | 100 | 100 | 100 | 100 | 100 | 100 | 100 |
| 118 | 96.0 | 100.0 | 100.5 | 96.4 | 104.8 | 91.6 | 97.3 | 100.7 | 93.3 | 94.5 | 101.6 | 101.4 | 98.2 | 99.0 |
| 174 | 99.2 | 102.6 | 104.2 | 100.1 | 98.1 | 88.9 | 100.2 | 103.1 | 94.6 | 96.5 | 98.0 | 105.1 | 101.1 | 100.9 |
| 279 | 93.2 | 91.8 | 91.2 | 94.0 | 81.2 | 76.5 | 98.6 | 93.3 | 82.5 | 81.9 | 91.6 | 93.5 | 88.4 | 93.4 |

TABLE 6

37 C
Activities by AAPF-pNA Assay in $\Delta AU\ min^{-1}ml^{-1}$

| Day | Buffer 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| 0 | 323 | 327 | 63.3 | 63.7 | 63.8 | 66.4 | 63.4 | 66.5 | 65.3 | 66.9 | 65.4 | 63.5 | 64.9 | 63.2 |
| 9 | 313 | 316 | 63.1 | 64.0 | 64.3 | 64.2 | 62.7 | 63.0 | 61.6 | 64.1 | 60.7 | 61.4 | 62.4 | 61.2 |
| 29 | 311 | 320 | 63.3 | 63.2 | 64.1 | 63.4 | 62.3 | 64.4 | 60.4 | 64.3 | 61.1 | 61.7 | 62.7 | 61.4 |
| 112 | 269 | 298 | 57.9 | 55.3 | 62.4 | 48.4 | 64.7 | 63.4 | 48.9 | 62.2 | 60.9 | 58.9 | 57.4 | 56.5 |
| 173 | 281 | 233 | 54.7 | 50.3 | 57.3 | 12.4 | 61.7 | 64.6 | 27.7 | 60.7 | 61.7 | 55.9 | 52.8 | 52.6 |
| 280 | 242 | 43.9 | 48.3 | 44.6 | 6.79 | 4.42 | 56.9 | 58.3 | 4.76 | 32.3 | 52.5 | 55.5 | 47.1 | 42.4 |

| % Original Activity Day | Buffer B1 | B2 | B3 | B4 | B5 | B6 | B7 | B8 | B9 | B10 | B11 | B12 | B13 | B14 |
|---|---|---|---|---|---|---|---|---|---|---|---|---|---|---|
| 0 | 100 | 100 | 100 | 100 | 100 | 100 | 100 | 100 | 100 | 100 | 100 | 100 | 100 | 100 |
| 9 | 97.0 | 96.6 | 99.8 | 100.5 | 100.7 | 96.9 | 98.9 | 94.7 | 94.4 | 95.8 | 92.8 | 96.7 | 96.2 | 96.8 |
| 29 | 96.4 | 97.7 | 100.0 | 99.2 | 100.4 | 95.4 | 98.1 | 96.9 | 92.5 | 96.0 | 93.4 | 97.2 | 96.7 | 97.1 |
| 112 | 83.4 | 90.9 | 91.4 | 86.9 | 97.8 | 72.9 | 102.0 | 95.4 | 75.0 | 93.0 | 93.2 | 92.7 | 88.4 | 89.4 |
| 173 | 87.0 | 71.2 | 86.4 | 79.0 | 89.8 | 18.7 | 97.3 | 97.1 | 42.5 | 90.7 | 92.9 | 97.2 | 86.1 | 83.3 |
| 280 | 75.1 | 13.4 | 76.3 | 70.0 | 10.6 | 6.6 | 89.6 | 87.7 | 7.3 | 48.3 | 80.3 | 87.4 | 72.6 | 67.1 |

Protease Assay

Examples 1 and 2 measured activity utilizing a protease assay with N-succinyl-L-Ala-L-L-Ala-L-Pro-L-Phe-p-nitroanilide (suc-AAPF-pNA). The assay is based upon the cleavage by proteases of the amide bond between phenylalanine and p-nitroaniline of the N-succinyl reagent. P-nitroaniline is monitored spectrophotometrically at 410 nm and the rate of the appearance of p-nitroaniline is a measure of proteolytic activity. A protease unit is defined as the amount of protease enzyme that increases absorbance at 410 nm by 1 absorbance unit (AU)/min of a standard solution of 1.6 mM suc-AAPF-pNA in 0.1 M Tris Buffer at 25° C. in a cuvet with a 1 cm path length. The glycerol was obtained from JT Baker.

Various other examples and modifications of the foregoing description and examples will be apparent to a person skilled in the art after reading the disclosure without departing from the spirit and scope of the invention, and it is intended that all such examples or modifications be included within the scope of the appended claims. All publications and patents referenced herein are hereby incorporated by reference in their entirety.

The invention claimed is:

1. A method for stabilizing one or more protease enzymes produced from *Bacillus* species in a liquid enzyme formulation, consisting of:
    formulating a liquid enzyme formulation consisting of at least about 4%, preferably at least about 5%, and most preferably between from about 5% to about 12% of an alkali metal halide salt in combination with a polyol solvent selected from the group consisting of glycerol, propylene glycol, sucrose, and any combination thereof, and one or more protease enzymes having at least about 95% activity remaining, preferably at least about 98% activity remaining after 22 days at 37° C. in the liquid enzyme formulation.

2. The method of claim 1, wherein said alkali metal halide salt comprises sodium chloride.

3. The method of claim 1, wherein said polyol is present at a level of at least about 50%, preferably between from about 50 to about 80%.

4. The method of claim 1, wherein said one or more protease enzymes is a subtilisin.

5. The method of claim 1, wherein said liquid enzyme formulation is a liquid enzyme concentrate.

6. The method of claim 1, wherein said polyol is present at a level of at least about 50%, preferably between from about 50 to about 80%.

7. A stabilized liquid enzyme formulation, consisting of:
    (i) a protease produced from any *Bacillus* species,
    (ii) at least about 5% of an alkali metal halide salt, and
    (iii) at least about 50% of a polyol solvent selected from glycerol, propylene glycol, sucrose, and any combination thereof, wherein said protease has at least about 95% activity remaining, preferably at least about 98% activity remaining, after 22 days at 37 degrees C. in the stabilized liquid enzyme formulation.

8. The formulation of claim 7, wherein said alkali metal salt comprises sodium chloride.

9. The formulation of claim 7, wherein said polyol solvent comprises propylene glycol.

10. The formulation of claim 7, wherein the polyol solvent comprises propylene glycol and glycerol.

11. The formulation of claim 7, wherein said protease is a subtilisin.

12. The formulation of claim 11, wherein said subtilisin includes an amino acid substitution at position 217.

* * * * *